(12) United States Patent
Tomoda et al.

(10) Patent No.: US 8,378,125 B2
(45) Date of Patent: Feb. 19, 2013

(54) SUBSTANCE FKI-3864 AND METHOD FOR PREPARATION THEREOF

(75) Inventors: Hiroshi Tomoda, Tokyo (JP); Ryuji Uchida, Tokyo (JP); Rokuro Masuma, Tokyo (JP); Satoshi Omura, Tokyo (JP)

(73) Assignee: School Juridical Person Kitasato Institute, Tokyo (JP)

( * ) Notice: Subject to any disclaimer, the term of this patent is extended or adjusted under 35 U.S.C. 154(b) by 72 days.

(21) Appl. No.: 12/867,435

(22) PCT Filed: Feb. 12, 2009

(86) PCT No.: PCT/JP2009/052271
§ 371 (c)(1),
(2), (4) Date: Dec. 1, 2010

(87) PCT Pub. No.: WO2009/101956
PCT Pub. Date: Aug. 20, 2009

(65) Prior Publication Data
US 2011/0105769 A1    May 5, 2011

(30) Foreign Application Priority Data
Feb. 13, 2008    (JP) .................................. 2008-032172

(51) Int. Cl.
*C07D 311/78*    (2006.01)
(52) U.S. Cl. ..................................................... 549/280
(58) Field of Classification Search .................. 549/280
See application file for complete search history.

(56) References Cited

FOREIGN PATENT DOCUMENTS

| JP | 08182496 A | 7/1996 |
|---|---|---|
| WO | 9941265 A1 | 8/1999 |
| WO | 0058491 A1 | 10/2000 |

OTHER PUBLICATIONS

Satoru Ote et al., "Shinkin FKI-3864 Kabu no Seisan suru Shinki Triacylglycerol Seisei Sogai Busshitsu ni Kansuru Kenkyu", Abstracts of 128th Annual Meeting of Pharmaceutical Society of Japan 2, Mar. 5, 2008, p. 127.

*Primary Examiner* — Nizal Chandrakumar
(74) *Attorney, Agent, or Firm* — The Webb Law Firm

(57) ABSTRACT

This invention relates to substance FKI-3864 represented by the following formula [I] having an inhibitory activity on the synthesis of triacylglycerols and a method for preparing the same. The substance FKI-3864 can be prepared by a method comprising culturing a microorganism which belongs to the genus *Penicillium* and is capable of producing the substance FKI-3864, and particularly *Penicillium pinophilum* FKI-3864 (FERM BP-11093) so as to accumulate the substance FKI-3864 in the culture and collecting the substance FKI-3864 from the culture. The substance has an inhibitory activity on the synthesis of intracellular triacylglycerols and is useful for prevention or treatment of obesity.

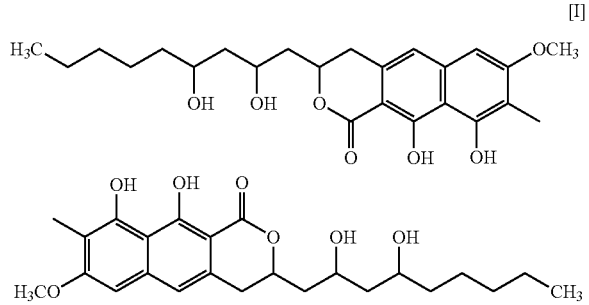

6 Claims, 12 Drawing Sheets

SUBSTANCE FKI-3864 AND METHOD FOR PREPARATION THEREOF

BACKGROUND OF THE INVENTION

1. Field of the Invention

The present invention relates to a novel substance, the substance FKI-3864 which is useful for prevention and treatment of obesity and associated diseases through inhibition of the synthesis of intracellular triacylglycerols and a method of preparing the same. The present invention also relates to a novel microorganism capable of producing the substance FKI-3864 and a use of the substance FKI-3864.

2. Description of Related Art

Obesity is a condition in which excess neutral fat, mainly in the form of triacylglycerols, has accumulated in the adipose tissue due to excessive energy intake. In an obese subject, hypertrophy of the adipose tissue produces dysregulation of adipocytokines and as a result causes impaired glucose tolerance and hyperlipemia. Therefore, obesity is considered to be a significant risk factor of so-called lifestyle-related diseases such as hyperlipemia, diabetes, and hypertension.

Antiobestic drugs which are currently used include centrally-acting anorectic drugs such as mazindol (Novartispharma) which is a noradrenergic agent, sibutramine (Eisai) which is a serotonin noradrenarin reuptake inhibitor, and rimonabant (Sanofi-aventis) which is a cannabinoid receptor antagonist and a pancreatic lipase inhibitor such as orlistat (Chugai Pharmaceutical). Centrally-acting anorectic drugs cause appetite suppression, thereby leading to a reduction in lipid absorption, but they sometimes impair the health of a subject due to their anorectic activity and may produce side effects such as thirst, constipation, auditory hallucination, visual hallucination, and dependency. A pancreatic lipase inhibitor may cause side effects in the digestive tract such as diarrhea, incontinence, and steatorrhea. Accordingly, it is desired to develop a novel antiobestic drug having no side effects.

In view of the fact that excessive accumulation of triacylglycerols in the adipose tissue causes obesity, a substance which inhibits the biosynthesis of triacylglycerols is expected to exhibit an antiobestic activity having a mechanism which is different from that of existing drugs.

With respect to a substance inhibiting accumulation of triacylglycerols, it is reported that a substance having an inhibitory activity on a diacylglycerol acyltransferase is produced by a microorganism (Patent Documents 1, 2, and 3).
Patent Document 1: JP 08-182496 A1
Patent Document 2: WO 99/41265 A1
Patent Document 3: WO 00/58491 A1

SUMMARY OF THE INVENTION IS TO SOLVE

It is an object of the present invention to provide a novel substance having a stronger inhibitory activity on the synthesis of triacylglycerols. Another object of the present invention is to provide a pharmaceutical preparation which is useful for prevention and treatment of obesity.

DETAILED DESCRIPTION OF THE INVENTION

Figure 1:
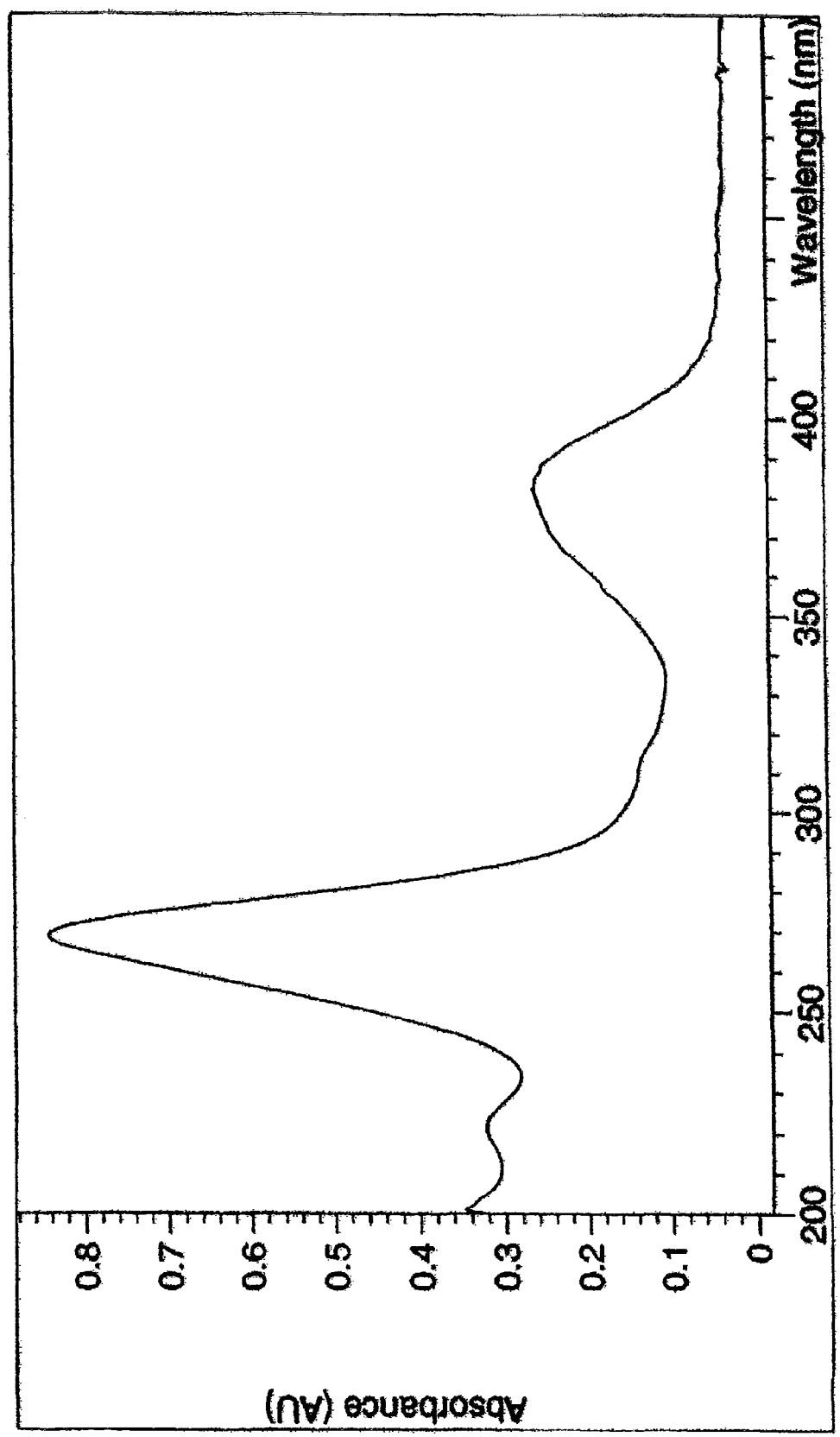
FIG. 1 shows an ultraviolet absorption spectrum (in a methanol solution) of substance FKI-3864 according to the present invention.

As a result of a search for triacylglycerol synthesis inhibitors among metabolites produced by microorganisms, the present inventors found that a substance having an inhibitory activity on the synthesis of triacylglycerols was produced in a culture of a filamentous fungus (mould) strain, FKI-3864 which had freshly been isolated from the soil. Subsequently, they isolated from the culture the substance having an inhibitory activity on the synthesis of triacylglycerols and purified, and they identified it as a novel substance having the chemical structure given below, which is now referred to as substance FKI-3864.

The present invention was completed based on these findings and it relates to substance FKI-3864 which is a compound having the following formula [I].

[I]

$$\text{H}_3\text{C}\text{-chain-OH-OH-O-(fused ring system)-OCH}_3\text{-OH-OH-O-(fused ring system)-OH-OH-chain-CH}_3$$

The present invention also relates to the above-mentioned substance FKI-3864 which is a compound having the following formula [II] and/or a compound having the following formula [III].

ing) a microorganism which belongs to the genus *Penicillium* and is capable of producing the substance FKI-3864 in a medium to cause the substance FKI-3864 to accumulate in the culture and collecting the substance FKI-3864 from the

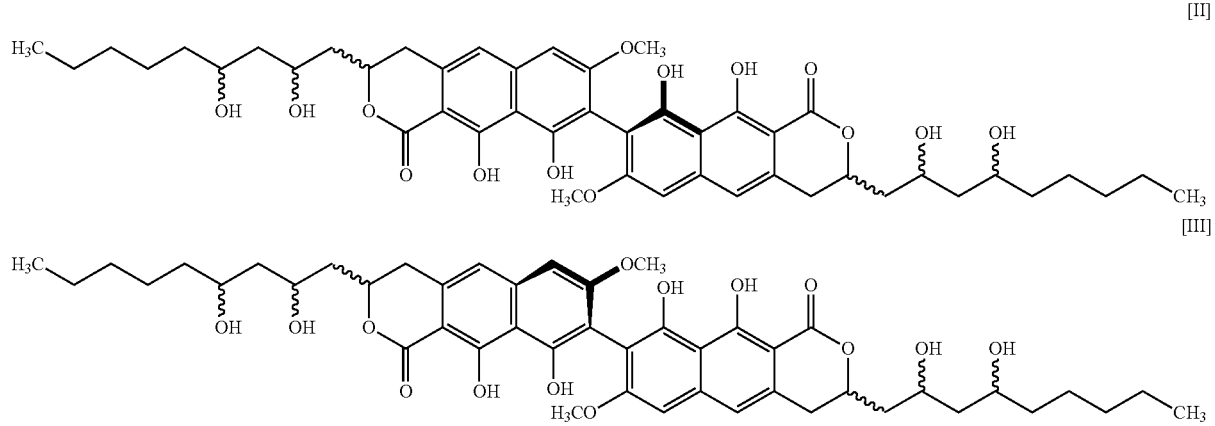

The present invention also relates to a method of preparing the novel substance FKI-3864 characterized by culturing a microorganism which belongs to the genus *Penicillium* and is capable of producing the substance FKI-3864 in a medium to accumulate the substance FKI-3864 in the culture and collecting the substance FKI-3864 from the culture. The microorganism which is used in this method is preferably *Penicillium pinophilum* FKI-3864 (FERM BP-11093).

The present invention also relates to a microorganism which belongs to the genus *Penicillium* and is capable of producing the substance FKI-3864 and in particular the microorganism *Penicillium pinophilum* FKI-3864 (FERM BP-11093).

EFFECT OF THE INVENTION

In accordance with the present invention, the novel substance FKI-3864 which inhibits the synthesis of intracellular triacylglycerols can be provided. The substance is expected to be useful as a drug for prevention or treatment of obesity caused by accumulation of triacylglycerols and diseases resulting from obesity. In addition, the present invention provides a microorganism which belongs to the genus *Penicillium* and is capable of producing the substance FKI-3864 and in particular the microorganism *Penicillium pinophilum* strain FKI-3864 (FERM BP-11093).

MODES FOR CARRYING OUT THE INVENTION

The substance FKI-3864 according to the present invention can be prepared by a method comprising culturing (incubatculture. An example of a strain which is used for the production of the substance FKI-3864 includes the strain *Penicillium pinophilum* FKI-3864 which was first isolated from the soil by the present inventors.

This strain has the following mycological characteristics.

1. Morphologic Characteristics

This strain grew well on a Czapek yeast extract agar medium, a malt extract agar medium, a potato carrot agar medium, or the like and showed good adhesion of conidospores (conidia) on various agar media.

When observed under a microscope, colonies grown on a Czapek yeast extract agar medium had hyphae which were colorless and had septa, and their conidophores (50-180×1.0-2.5 μm) formed upright from the aerial hyphae with no branches. At the tip of the conidophores, penicilli were formed. The penicilli were biverticillate and were constituted by 3-5 acervating phialides. The phialides were cylindrical and measured 7.5-12.5×2.0-2.5 μm. Phialoconidia were formed from the tip of the phialides and they became linked as the duration of incubation elapsed. The conidospores were globose or subglobose in shape and sage green in color, and they measured 2.3-2.8×2.3-2.8 μm and had smooth surfaces.

2. Properties of Cultures

The results of visual observation of cultures obtained by incubation for 7 days at 25° C. on various agar media are shown in Table 1.

TABLE 1

| Medium | State of growth on medium (diameter of colonies) | Color of colonies on the front side | Color of colonies on the reverse side | Soluble pigment |
|---|---|---|---|---|
| Czapek-yeast extract agar medium | Good (34-37 mm) velvety smooth periphery | Sage green with pale yellow periphery | Pale tan | None |
| 25% glycerin-nitrate agar medium | Suppressed (9-10 mm) floccose smooth periphery | White | Pale yellow | None |

TABLE 1-continued

| Medium | State of growth on medium (diameter of colonies) | Color of colonies on the front side | Color of colonies on the reverse side | Soluble pigment |
|---|---|---|---|---|
| Malt extract agar medium | Good (37-39 mm) floccose smooth periphery | Yellow | Yellow | None |
| Potato carrot agar medium | Good (39-40 mm) floccose smooth periphery | Sage green | Sage green | None |

3. Physiological Properties

1) Optimum Growth Conditions

The optimum growth conditions for the strain are a pH of 4-5 and a temperature of 26.1-35.7° C.

2) Growth Range

The growth range of the strain is a pH of 2-8 and a temperature of 14.4-37.8° C.

3) Identification as Aerobic or Anaerobic

Aerobic

As a result of an attempt to compare the present strain with known strains based on the above-mentioned morphologic characteristics, properties of cultures, and physiological properties, the strain was identified as a strain belonging to the genus *Penicillium pinophilum* and was denominated *Penicillium pinophilum* FKI-3864. The present strain was originally deposited in the name of *Penicillium pinophilum* FKI-3864 at the International Patent Organism Depositary (IPOD) of the National Institute of Advanced Industrial Science and Technology located at Tsukuba Central 6, 1-1-1 Higashi, Tsukuba-shi, Ibaraki-ken, Japan) on Dec. 27, 2007 (Accession No: FERM P-21483). However, on Feb. 10, 2009, Accession No: FERM BP-11093 was assigned to the deposit under the Budapest Treaty.

In order to prepare the substance FKI-3864 according to the present invention, it is preferred to use the above-described strain *Penicillium pinophilum* FKI-3864. However, the microorganism which is used is not limited to this strain, and any microorganism, including an artificial or spontaneous mutant or variant of the above-described strain, which belongs to the genus *Penicillium* and is capable of producing the substance FKI-3864 can be used.

As a medium for culturing (incubating) the microorganism, a nutrient culture medium containing an assimilable carbon source (which can be assimilated by microorganisms), an assimilable nitrogen source, and optionally an inorganic salt, a vitamin or the like as nutrients can be used. As an assimilable carbon source, saccharides such as glucose, fructose, maltose, lactose, galactose, dextrin, and starch and vegetable oil and fat such as soybean oil can be used singly or in combination. As an assimilable nitrogen source, peptone, yeast extract, meat extract, soybean meal, cottonseed meal, corn steep liquor, malt extract, casein, an amino acid, urea, an ammonium salt, and a nitrate salt can be used singly or in combination. In addition, salts such as a phosphate, a magnesium salt, a calcium salt, a sodium salt, and a potassium salt, heavy metal salts such as an iron salt, a manganese salt, a copper salt, a cobalt salt, and a zinc salt, vitamins, and other additives which are suitable for the production of the substance FKI-3864 can be appropriately added as required.

If incubation (culturing) causes a heavy foam, an antifoaming agent such as liquid paraffin, an animal oil, a vegetable oil, a silicone, or a surfactant may be added to the medium as required. As long as the above-described nutrients are contained, the medium which is used for incubation may be liquid or solid. Usually it is preferable that incubation be carried out using a liquid medium. When the desired substance is mass-produced on a commercial scale, the aeration spinner culture method is preferably employed.

In the case where incubation is carried out in a large tank, it is preferred in order to prevent a delay in microorganism growth during the production process that a strain which is used to produce the desired substance be inoculated and cultured in a relatively small quantity of a medium and that the resulting culture then be transferred into the large tank where productive incubation is carried out. In this case, the medium used for the preincubation (preculture) may be the same as or different from that used for the productive incubation (productive culture).

When incubation is carried out under aeration and spinning (agitation) conditions, any appropriate known technique such as propeller agitation or other type of mechanical agitation, rotation or vibration of a fermenter, pumping, or air bubbling can be employed. Sterilized air should be used for aeration.

The incubation temperature can be appropriately varied within the range in which the strain used for producing the substance FKI-3864 produces the desired substance, and it is usually 20-30° C. and preferably around 27° C. It is preferred to use the shake culture or static culture method singly or both of these methods in combination.

The duration of incubation varies depending on the culture conditions, and it is usually on the order of 10-16 days in the case of a combination of shake culture and static culture.

The novel substance according to the present invention accumulated in the culture can be collected using a method which is conventionally used for collection of a metabolite from a microorganism culture. For example, the desired substance can be isolated and purified by a method such as extraction with an organic solvent, concentration, drying, adsorption, filtration, centrifugal separation, or chromatography.

The substance FKI-3864 according to the present invention can be collected from a culture of the strain *Penicillium pinophilum* FKI-3864 by a method comprising extracting the entire culture with a water-miscible organic solvent such as ethanol, distilling off the organic solvent from the extract at a reduced pressure, and then extracting the residue with a water-immiscible organic solvent such as ethyl acetate. In addition to these extraction techniques, known techniques which are used to collect a fat-soluble substance such as adsorption chromatography, gel filtration chromatography, thin layer chromatography, centrifugal counter-current distribution chromatography, and high performance liquid chromatography may appropriately be combined or repeated to isolate and purify the substance FKI-3864.

The physicochemical properties of substance FKI-3864 which was obtained in this manner are given below.

Figure 2:
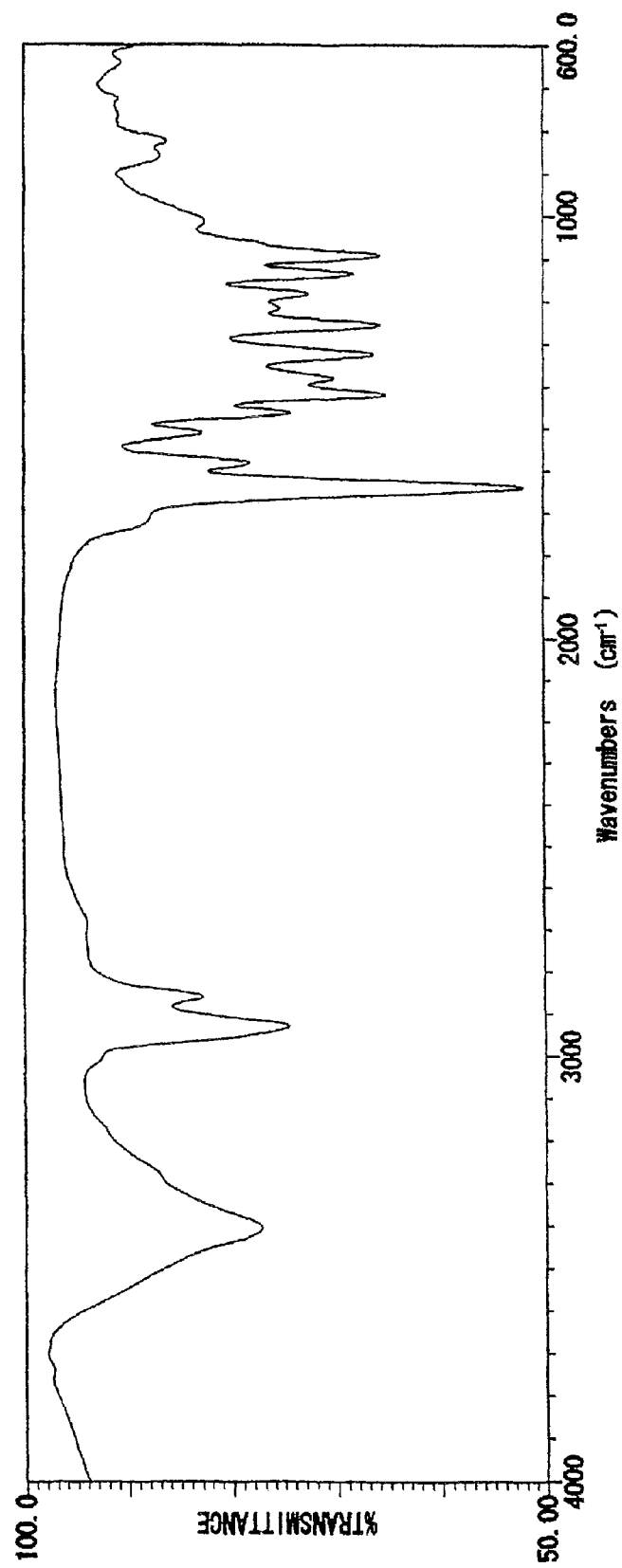
FIG. 2 shows an infrared absorption spectrum (the potassium bromide method) of substance FKI-3864 according to the present invention.
Figure 3:
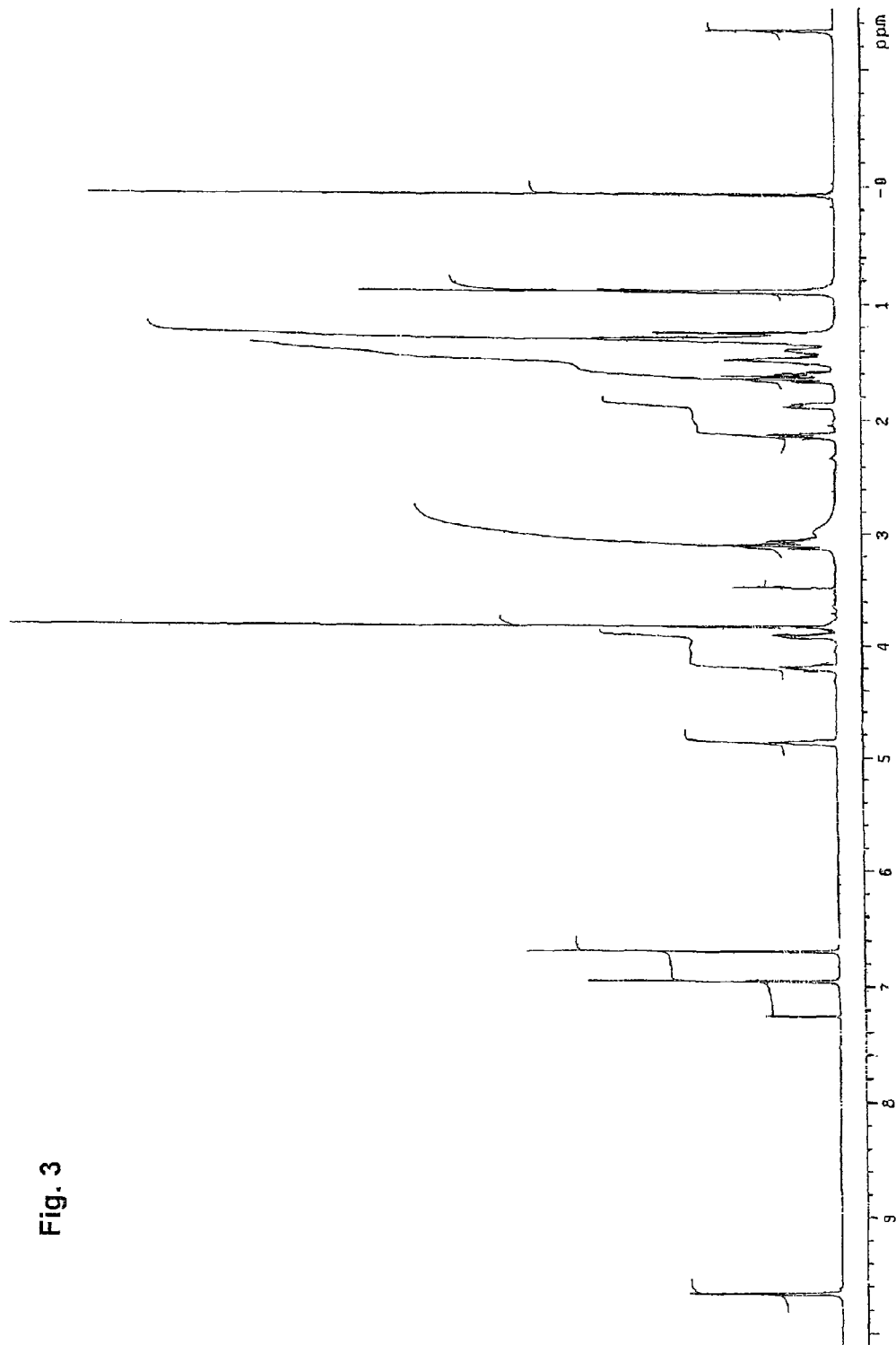
FIG. 3 shows a proton nuclear magnetic resonance spectrum (the deuterochloroform method) of substance FKI-3864 according to the present invention.
Figure 4:
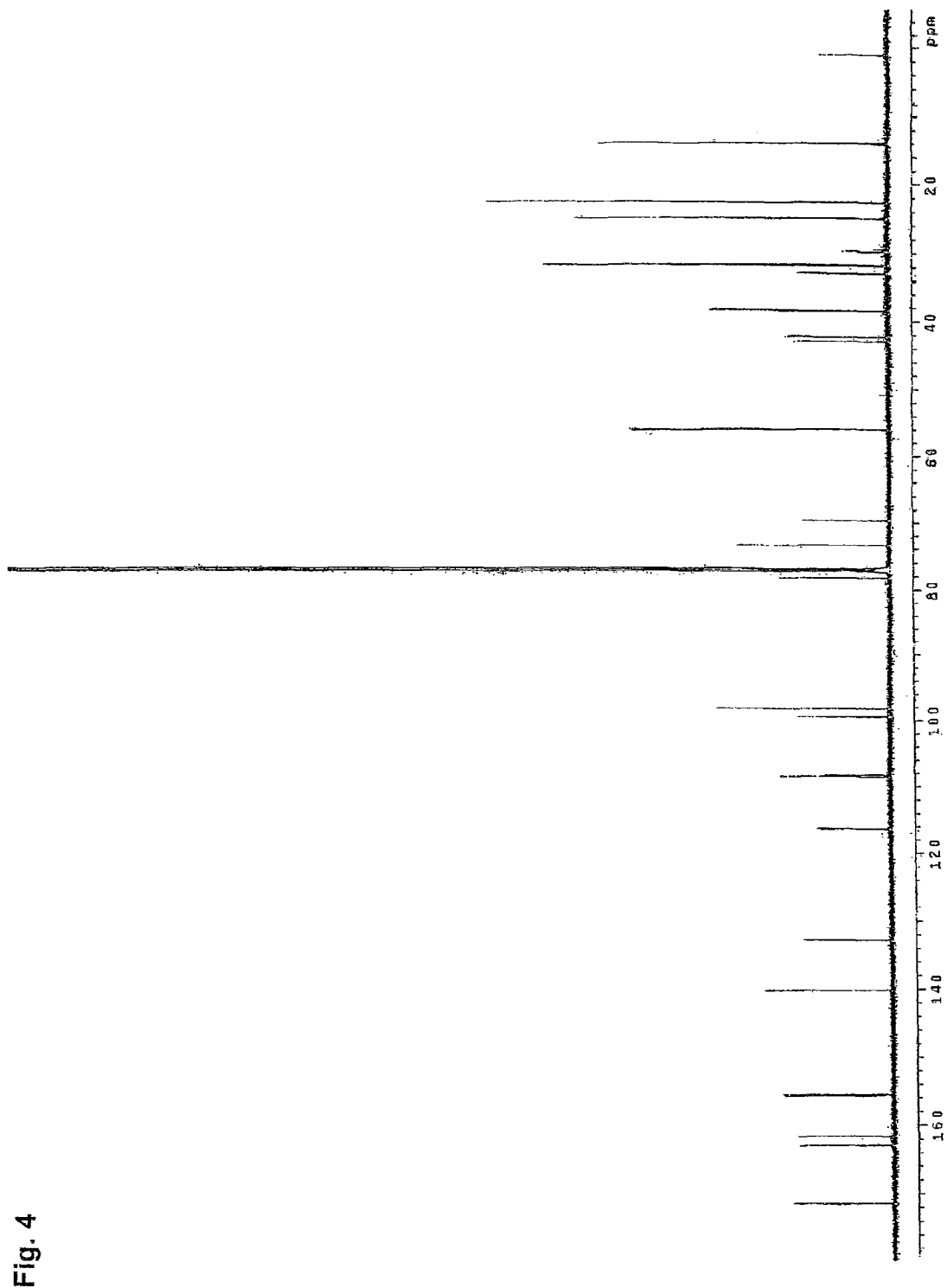
FIG. 4 shows a carbon nuclear magnetic resonance spectrum (the deuterochloroform method) of substance FKI-3864 according to the present invention.

(1) Appearance: yellow powder.
(2) Molecular formula: $C_{46}H_{58}O_{14}$
HRFAB-MS (m/z) $[M+H]^+$ calculated: 835.3905. found: 835.3934.
(3) Molecular weight: 834
$[M+H]^+$ 835 was observed in FAB-MS (m/z).
(4) Ultraviolet absorption spectrum:
An ultraviolet absorption spectrum measured in a methanol solution is shown in FIG. 1. λmax (MeOH, ε): 222 (26667), 269 (70000), 382 (21667).
(5) Infrared absorption spectrum:
An infrared absorption spectrum measured by the potassium bromide tablet method is shown in FIG. 2. Characteristic absorption maxima appear at νmax 3398, 2924, 1637 $cm^{-1}$.
(6) Specific rotation: $[\alpha]_D^{26}$ +65.6° (c=0.1, methanol).
(7) Solubility in solvents: Soluble in methanol, chloroform, and ethyl acetate; insoluble in water.
(8) Proton and carbon nuclear magnetic resonance spectra: The hydrogen chemical shifts (ppm) and carbon chemical shifts (ppm) measured in deuterochloroform using a 600 MHz nuclear magnetic resonance spectrometer manufactured by Varian are as follows.
$\delta_H$: 0.89 (3H), 1.30 (6H), 1.49 (2H), 1.63 (2H), 1.88 (1H), 2.13 (1H), 3.09 (2H), 3.83 (3H), 3.92 (1H), 4.20 (1H), 4.87 (1H), 6.70 (1H), 6.96 (1H), 9.67 (1H) ppm;
$\delta_C$: 14.0, 22.6, 24.9, 31.7, 32.8, 38.3, 42.3, 42.9, 55.9, 69.5, 73.2, 78.1, 98.1, 99.3, 108.2, 108.4, 116.2, 132.7, 140.1, 155.4, 161.5, 162.8, 171.3 ppm.

As a result of a detailed investigation of the above-described various physicochemical properties and spectral data of substance FKI-3864, substance FKI-3864 was determined to have the chemical structure represented by the following formula [I].

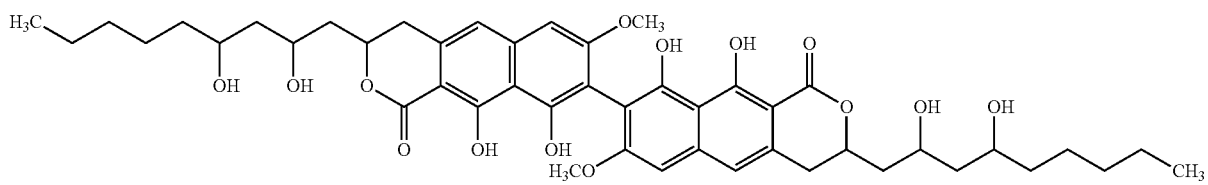

[I]

The substance FKI-3864 can be separated into two stereoisomers FKI-3864-1 and FKI-3864-2 by a separation technique such as adsorption chromatography or high performance liquid chromatography.

Figure 5:
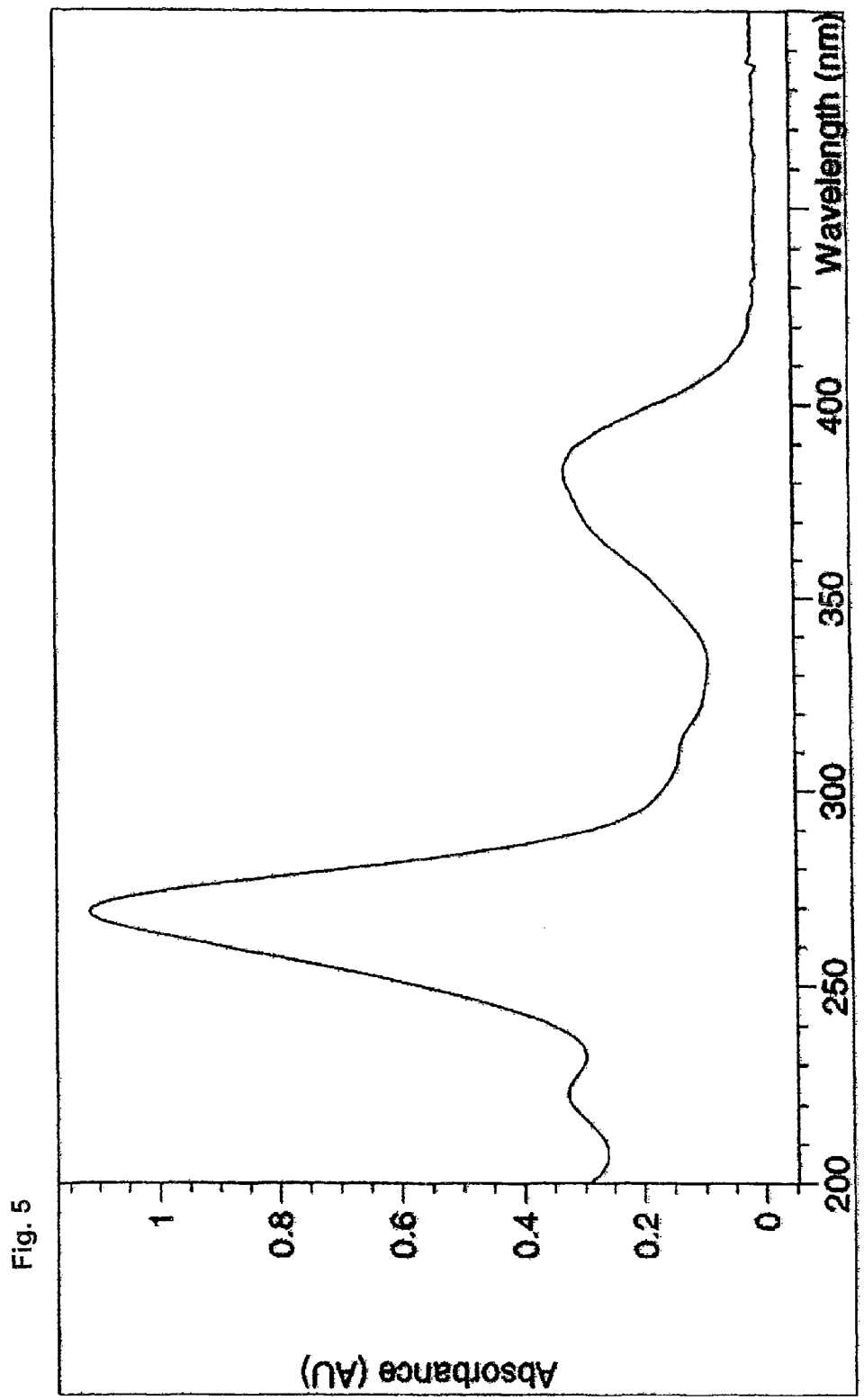
FIG. 5 shows an ultraviolet absorption spectrum (in a methanol solution) of substance FKI-3864-1 according to the present invention.
Figure 6:
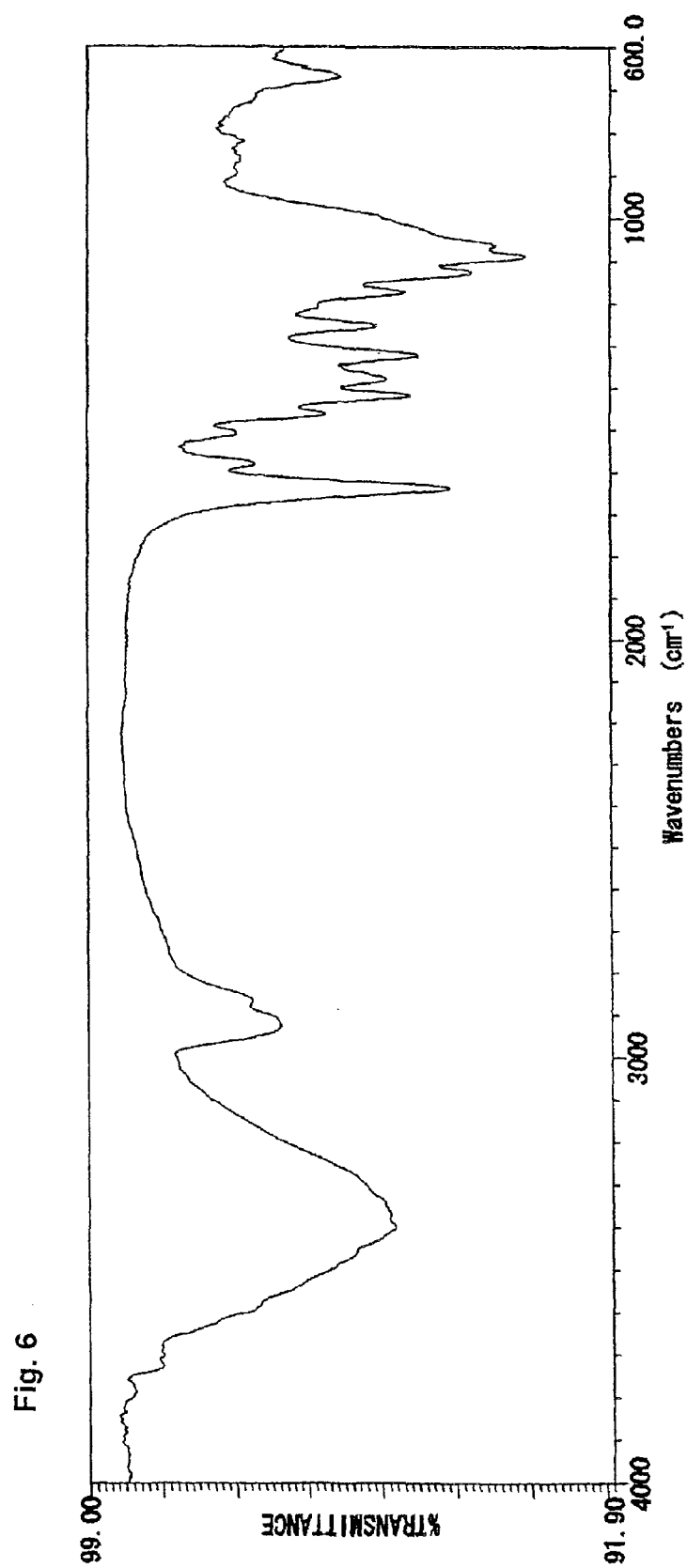
FIG. 6 shows an infrared absorption spectrum (the potassium bromide method) of substance FKI-3864-1 according to the present invention.
Figure 7:
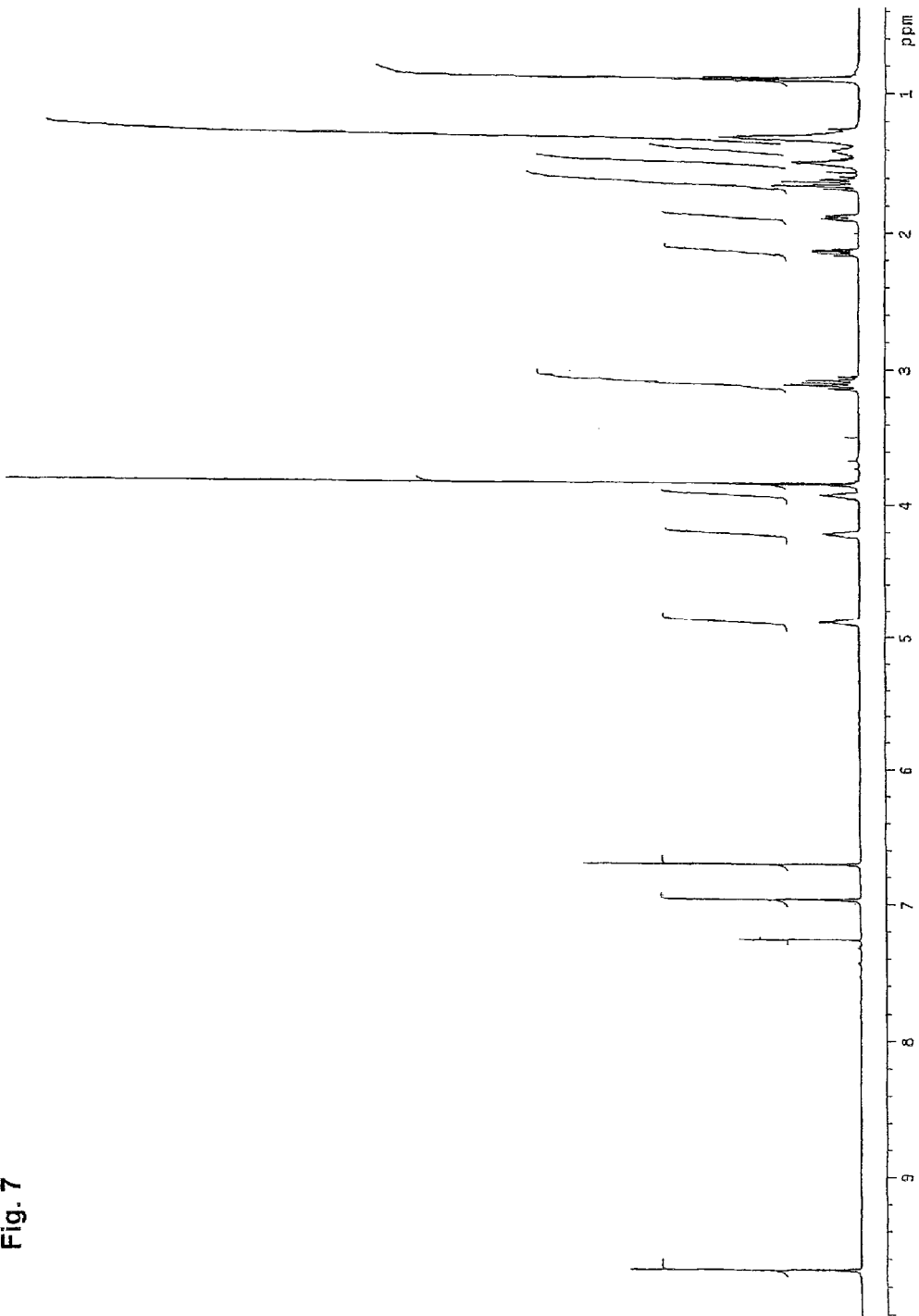
FIG. 7 shows a proton nuclear magnetic resonance spectrum (the deuterochloroform method) of substance FKI-3864-1 according to the present invention.
Figure 8:
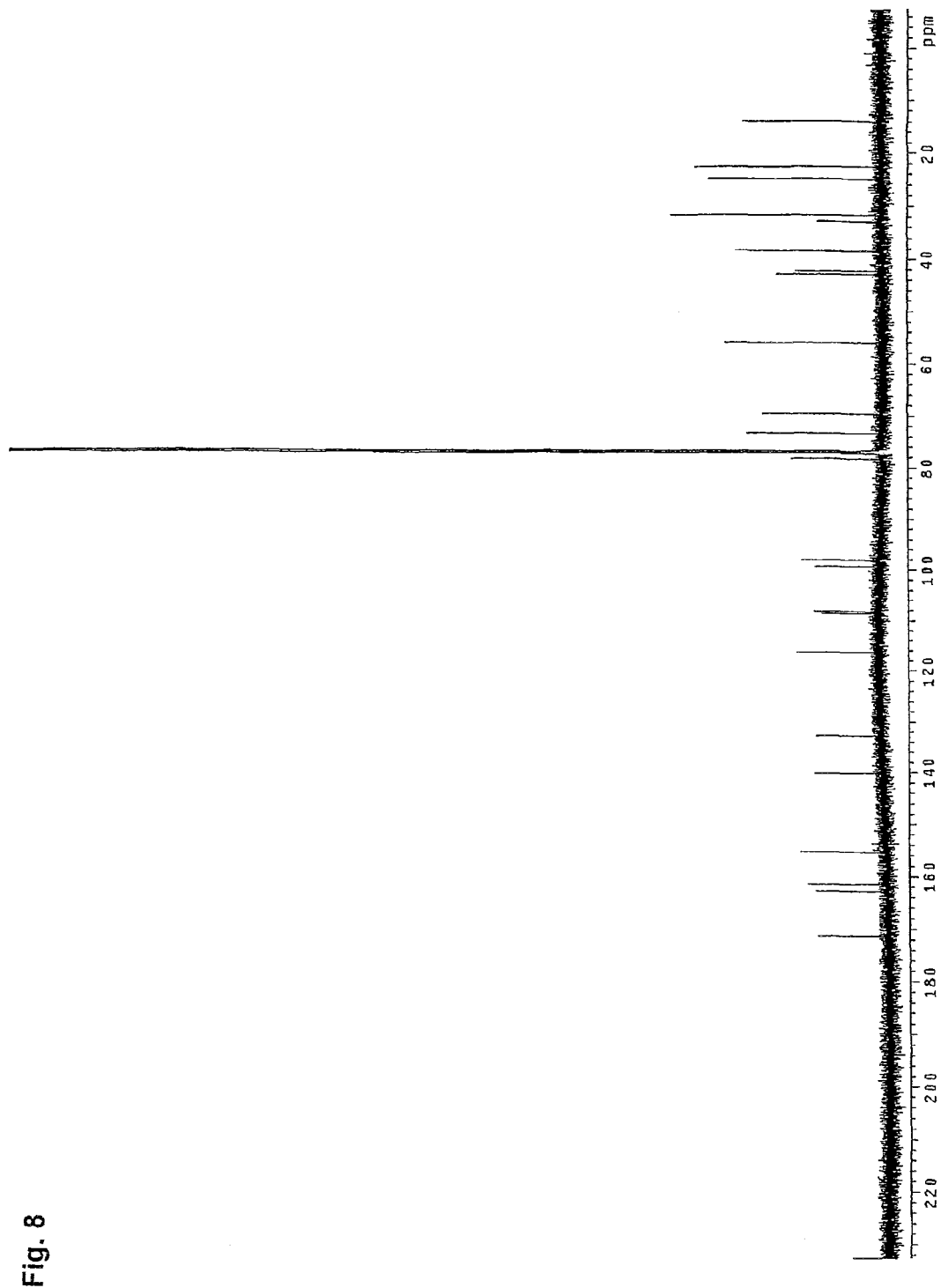
FIG. 8 shows a carbon nuclear magnetic resonance spectrum (the deuterochloroform method) of substance FKI-3864-1 according to the present invention.

The physicochemical properties of substance FKI-3864-1 according to the present invention are given below.
(1) Appearance: yellow powder.
(2) Molecular formula: $C_{46}H_{58}O_{14}$
HRFAB-MS (m/z) $[M+H]^+$ calculated: 835.3905. found: 835.3923.
(3) Molecular weight: 834
$[M+H]^+$ 835 was observed in FAB-MS (m/z).
(4) Ultraviolet absorption spectrum:
An ultraviolet absorption spectrum measured in a methanol solution is shown in FIG. 5. λmax (MeOH, ε): 222 (27250), 269 (93000), 382 (27250).
(5) Infrared absorption spectrum:
An infrared absorption spectrum measured by the potassium bromide tablet method is shown in FIG. 6. Characteristic absorption maxima appear at νmax 3403, 2929, 1639 $cm^{-1}$.
(6) Specific rotation: $[\alpha]_9^{26}$ −190.1° (c=0.1, methanol).
(7) Solubility in solvents: Soluble in methanol, chloroform, and ethyl acetate; insoluble in water.
(8) Proton and carbon nuclear magnetic resonance spectra: The hydrogen chemical shifts (ppm) and carbon chemical shifts (ppm) measured in deuterochloroform using a 600 MHz nuclear magnetic resonance spectrometer manufactured by Varian are as follows.
$\delta_H$: 0.90 (3H), 1.30 (6H), 1.49 (2H), 1.63 (2H), 1.89 (1H), 2.14 (1H), 3.10 (2H), 3.84 (3H), 3.93 (1H), 4.22 (1H), 4.88 (1H), 6.71 (1H), 6.97 (1H), 9.68 (1H) ppm;
$\delta_C$: 14.0, 22.6, 24.9, 31.7, 33.0, 38.4, 42.2, 42.9, 55.9, 69.6, 73.3, 78.2, 98.1, 99.3, 108.2, 108.4, 116.3, 132.7, 140.1, 155.4, 161.5, 162.9, 171.3 ppm.
(9) Circular dichroism spectrum: λext (MeOH, Δε): 280 (−71), 251 (+85).

Figure 9:
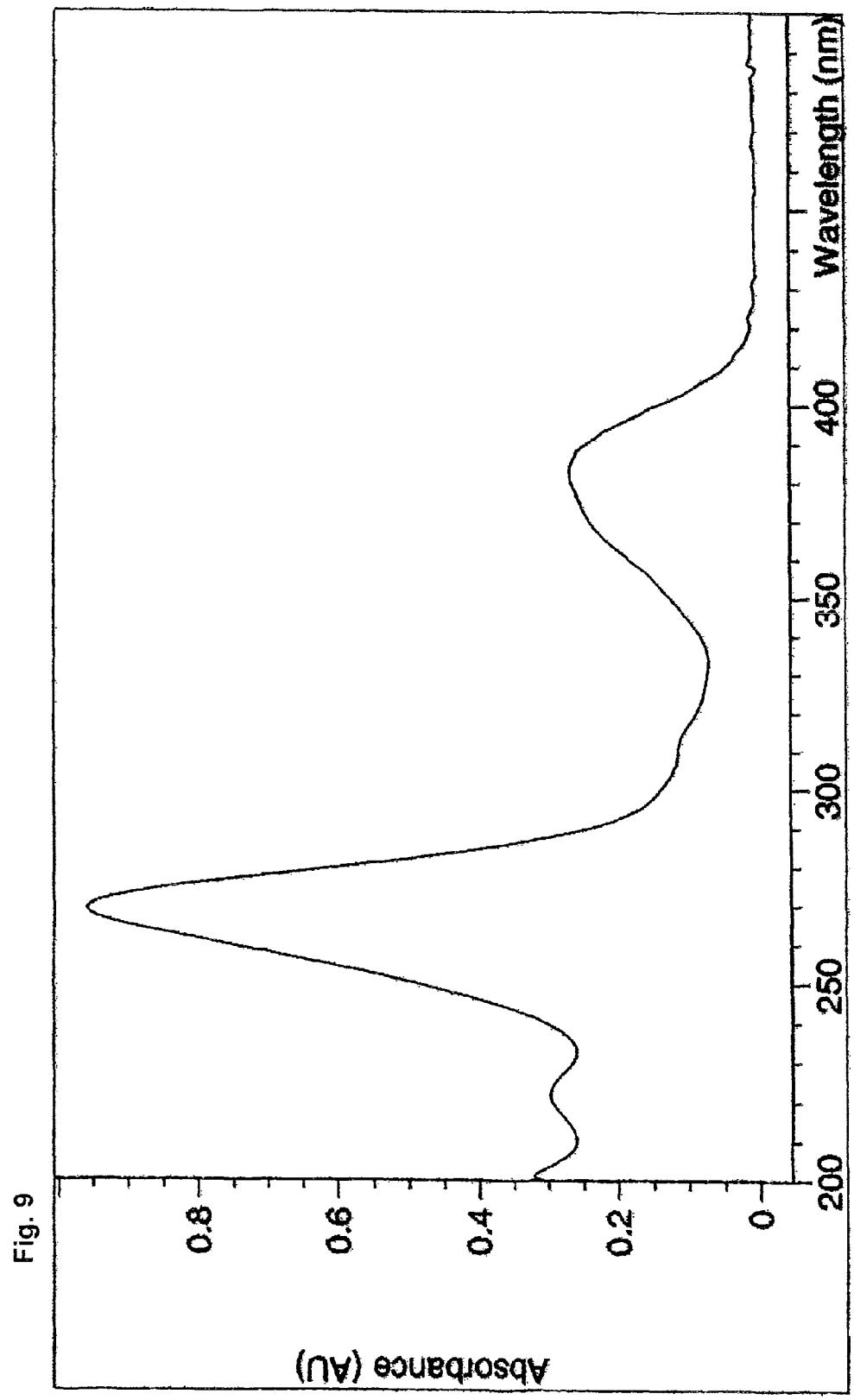
FIG. 9 shows an ultraviolet absorption spectrum (in a methanol solution) of substance FKI-3864-2 according to the present invention.
Figure 10:
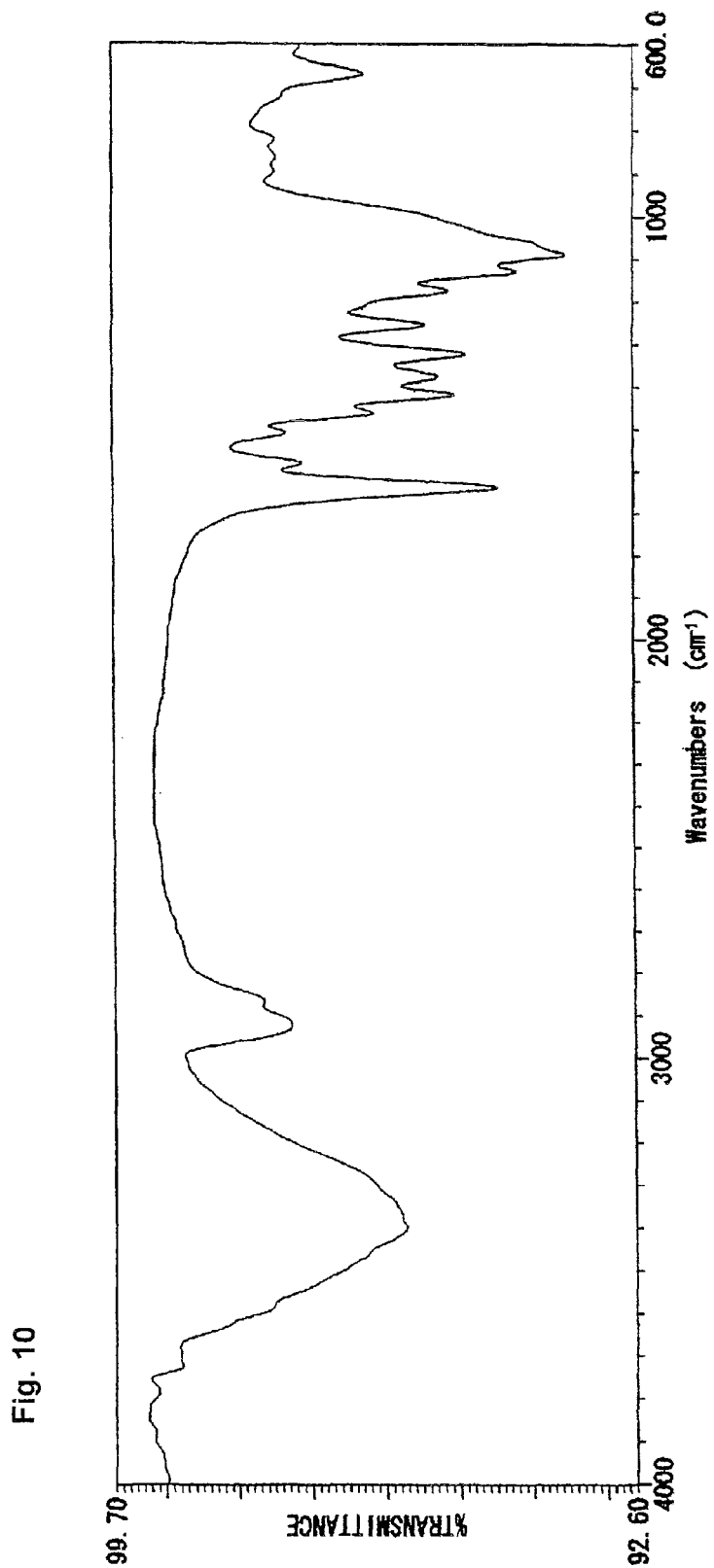
FIG. 10 shows an infrared absorption spectrum (the potassium bromide method) of substance FKI-3864-2 according to the present invention.
Figure 11:
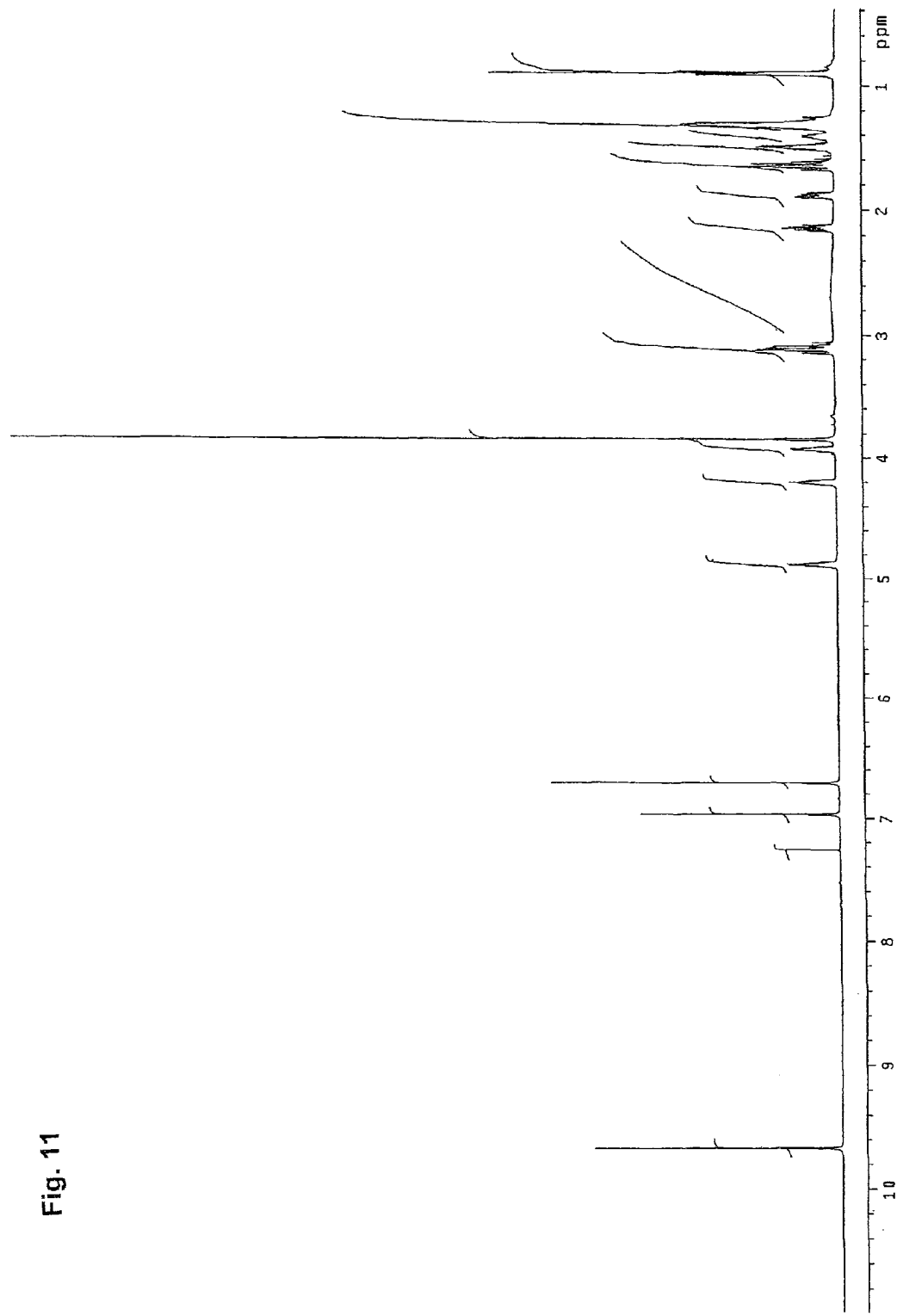
FIG. 11 shows a proton nuclear magnetic resonance spectrum (the deuterochloroform method) of substance FKI-3864-2 according to the present invention.
Figure 12:
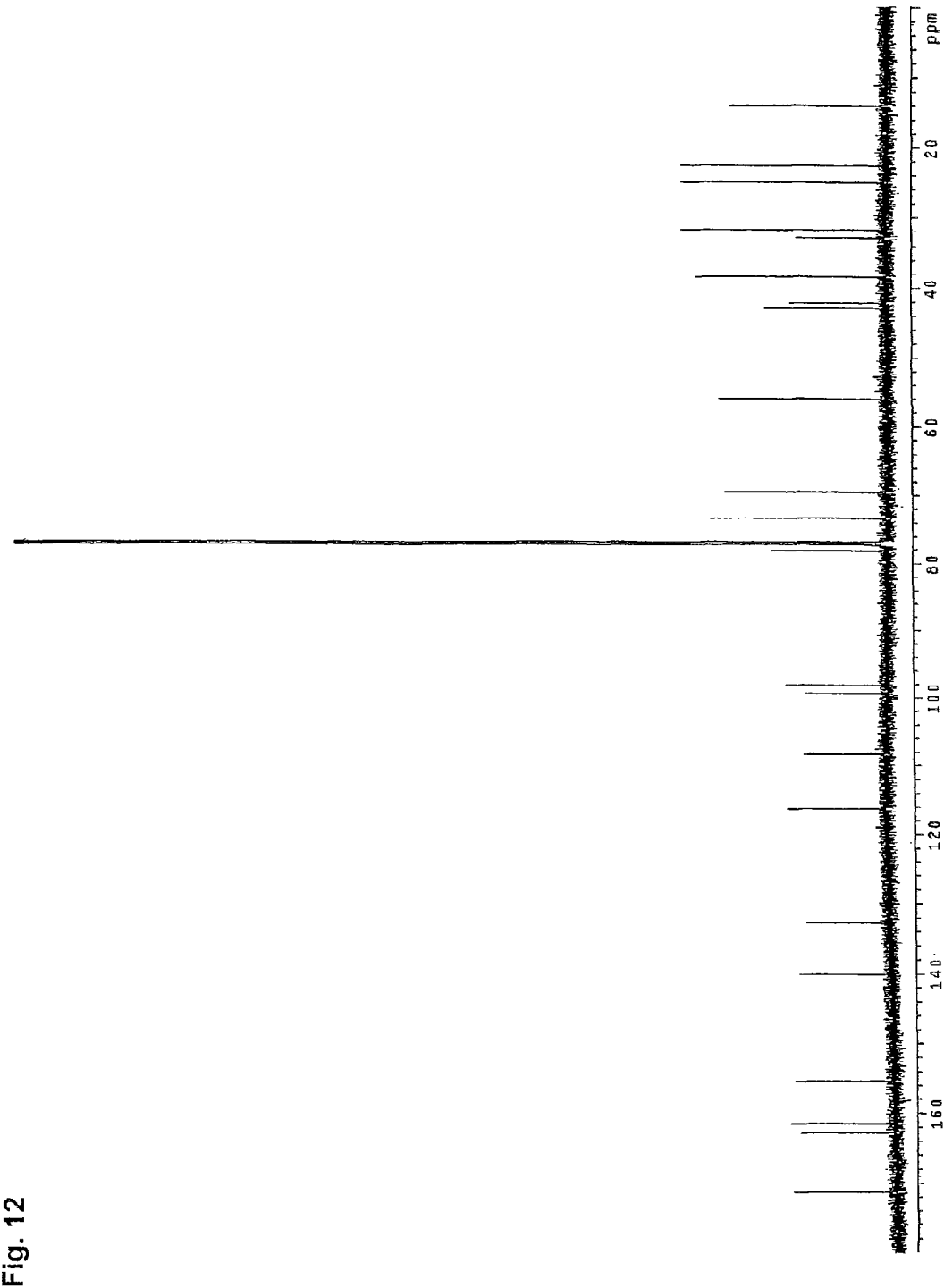
FIG. 12 shows a carbon nuclear magnetic resonance spectrum (the deuterochloroform method) of substance FKI-3864-2 according to the present invention.

Next, the physicochemical properties of substance FKI-3864-2 according to the present invention are given below.
(1) Appearance: yellow powder.
(2) Molecular formula: $C_{46}H_{58}O_{14}$
HRFAB-MS (m/z) $[M+H]^+$ calculated: 835.3905. found: 835.3934.
(3) Molecular weight: 834
$[M+H]^+$ 835 was observed in FAB-MS (m/z).
(4) Ultraviolet absorption spectrum:
An ultraviolet absorption spectrum measured in a methanol solution is shown in FIG. 9. λmax (MeOH, ε): 222 (24750), 269 (80000), 382 (22333).
(5) Infrared absorption spectrum:
An infrared absorption spectrum measured by the potassium bromide tablet method is shown in FIG. 10. Characteristic absorption maxima appear at νmax 3403, 2929, 1639 $cm^{-1}$.
(6) Specific rotation: $[\alpha]_D^{26}$ +246.3° (c=0.1, methanol).
(7) Solubility in solvents: Soluble in methanol, chloroform, and ethyl acetate; insoluble in water.
(8) Proton and carbon nuclear magnetic resonance spectra: The hydrogen chemical shifts (ppm) and carbon chemical shifts (ppm) measured in deuterochloroform using a 600 MHz nuclear magnetic resonance spectrometer manufactured by Varian are as follows.
$\delta_H$: 0.90 (3H), 1.30 (6H), 1.49 (2H), 1.63 (2H), 1.88 (1H), 2.14 (1H), 3.10 (2H), 3.85 (3H), 3.92 (1H), 4.20 (1H), 4.88 (1H), 6.71 (1H), 6.97 (1H), 9.67 (1H) ppm;
$\delta_C$: 14.0, 22.6, 24.9, 31.7, 32.8, 38.4, 42.1, 42.9, 56.0, 69.5, 73.4, 78.1, 98.1, 99.3, 108.2, 108.4, 116.3, 132.7, 140.1, 155.4, 161.5, 162.8, 171.3 ppm.
(9) Circular dichroism spectrum: λext (MeOH, Δε): 278 (+48), 255 (−69).

As described above, from the fact that the physicochemical properties and spectral data of substances FKI-3864-1 and FKI-3864-2 roughly correspond to those of substance FKI-3864 except that the data on specific rotation are totally different, FKI-3864-1 and FKI-3864-2 were expected to be stereoisomers. In addition, since the signs of the primary Cotton effect in the analysis of the circular dichroism spectra of these two substances were the reverse of each other, it was elucidated that FKI-3864-1 and FKI-3864-2 were steroisomers with respect to their shaft portion.

FKI-3864-1 and FKI-3864-2 are represented by the following structural formulas [II] and [III], respectively.

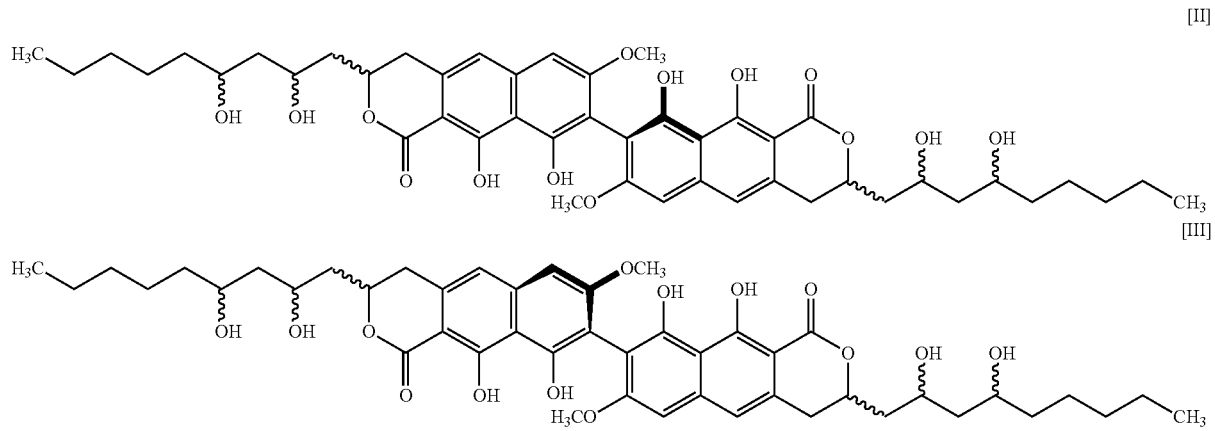

As shown by the below-described test, FKI-3864 according to the present invention has an inhibitory activity against the synthesis of intracellular triacylglycerols. In addition, each of FKI-3864-1 and FKI-3864-2 exhibits by itself an inhibitory activity against the synthesis of intracellular triacylglycerols. A mixture of these two isomers exhibits a different activity depending on the mixing ratio of the isomers, so it is possible to select and use a mixture of the isomers which exhibits an activity desirable for the end use. According to the below-described test, the strongest activity was exhibited when the isomers were mixed at a ratio of 1:1.

Accordingly, substance FKI-3864 as is without separation and FKI-3864-1 and FKI-3864-2 when used singly or as a mixture can be used for prevention or treatment of diseases attributable to excessive accumulation of intracellular triacylglycerols, such as obesity. In addition, they can be expected to be useful for prevention or treatment of lifestyle-related diseases caused by obesity such as hyperlipemia, diabetes, and hypertension.

When a novel compound according to the present invention is used as a pharmaceutical preparation, it is used as an active agent and is formulated in the form of a solution, suspension, tablet, granule, powder, capsule, or the like in a conventional manner by addition of a conventional carrier, an excipient, and if necessary a binder, a disintegrating agent, a lubricant, a buffer, a suspending agent, a stabilizer, a pH modifier, a colorant, a corrigent, a flavor, and the like.

The following examples are given to illustrate the present invention, but the present invention is not limited thereto.

Example 1

Preparation of Substance FKI-3864

100 mL aliquots of a seed medium (2% glucose (Wako Pure Chemical), 0.5% polypeptone (Wako Pure Chemical), 0.05% $MgSO_4.7H_2O$ (Wako Pure Chemical), 0.2% yeast extract (Oriental Yeast), 0.1% $KH_2PO_4$ (Kanto Chemical), 0.1% agar (Shimizu Shokuhin), adjusted to pH 6.0) which were separately poured into 500 mL Erlenmeyer flasks were each inoculated with one platinum loop of a culture of the strain FKI-3864 which had been incubated on an agar slant medium (0.1% glycerol (Kanto Chemical), 0.08% $KH_2PO_4$ (Kanto Chemical), 0.02% $K_2HPO_4$ (Kanto Chemical), 0.02% $MgSO_4.H_2O$ (Wako Pure Chemical), 0.02% KCl (Kanto Chemical), 0.2% $NaNO_3$ (Wako Pure Chemical), 0.02% yeast extract (Oriental Yeast), 1.5% agar (Shimizu Shokuhin), adjusted to pH 6.0) and were incubated at 27° C. for 3 days on a rotary shaker (at 210 rpm). The resulting cultures were each planted at a concentration of 1% into 1 L Raux flasks (30 flasks) each containing 200 mL of a productive medium (3.0% saccharose (Wako Pure Chemical), 1.0% soluble starch (Kanto Chemical), 0.3% malt extract (Sanko Junyaku), 0.5% $KH_2PO_4$ (Kanto Chemical), 0.05% $Mg(SO_4)_2.8H_2O$ (Kanto Chemical), adjusted to pH 6.0) and incubated at 27° C. for 13 days by the static culture method.

At the end of incubation, ethanol (6 L) was added to the combined culture (6 L) and an extract was obtained after stirring for 1 hour. Ethanol was distilled off from the extract at a reduced pressure to give 6 L of a concentrated liquor. From the concentrated liquor, an active ingredient was extracted with ethyl acetate (6 L), and the ethyl acetate layer was concentrated to dryness to give a crude active substance with a raw umber color (4.5 g). The crude substance was subjected to crude purification using a silica gel column (silica gel 60, Merck, 140 g). Chromatography was carried out using chloroform-methanol mixed solvents (100:0, 10:1, 1:1, 0:100) as developing solvents, and the eluate was collected in a 1 L fraction under each condition. The fraction containing substance FKI-3864 (10:1 fraction) was concentrated to give 1.9 g of a brown substance. This crude substance was again subjected to purification using a silica gel column (silica gel 60, Merck, 80 g). Chromatography was carried out using chloroform-methanol mixed solvents (100:0, 100:1, 50:1, 100:3, 20:1, 10:1, 0:100) as developing solvents, and the eluate was collected in a 400 mL fraction under each condition. The fractions containing substance FKI-3864 (chloroform-methanol 100:3, 10:1, and 0:100 fractions) were concentrated to give 866 mg of a tan substance. This substance was purified using an ODS column. Chromatography was carried out using each of mixed solvents of 50%, 60%, 70%, 80%, and 100% acetonitrile and an aqueous 0.05% $H_3PO_4$ solution as developing solvents, and the eluate was collected in a 120 mL fraction under each condition. The fraction containing substance FKI-3864 (the fraction of 80% acetonitrile-aqueous 0.05% $H_3PO_4$ solution) was concentrated at a reduced pressure, and the remaining aqueous solution was extracted with ethyl acetate to give 62 mg of a yellow substance. The substance was dissolved in a small amount of methanol and purified by preparative HPLC (column: PEGASIL ODS, 20φ×250 mm, Senshu Scientific). An isocratic mixed solvent of 80% acetonitrile-0.05% $H_3PO_4$ aqueous solution was used as a mobile phase, and UV absorption at 270 nm of the eluate was monitored at a flow rate of 8 mL/min. At a retention time of 17 min, a peak which shows activity was observed, and the eluate at this peak was collected. The collected solution was concentrated at a reduced pressure, and the remaining aqueous solution was extracted with ethyl acetate to isolate the desired substance FKI-3864 as a yellow powder with a yield of 16.7 mg.

(Test 1)

The inhibitory activity on the synthesis of intracellular triacylglycerols of substance FKI-3864 according to the invention was tested in the manner described below.

Chinese hamster ovary cells (CHO-K1 cells) adjusted to $5.0 \times 10^5$ cells/mL with HAMs F12 medium (10% FBS, containing Penicillin/Streptomycin) were distributed on a 48-well plate in aliquots of 250 μL.

Then, after the cells were incubated at 37° C. for 12 hours in a 5% carbon dioxide gas incubator to adhere the cells, substance FKI-3864 (2.5 μL as a methanol solution) and [1–$^{14}$C] oleic acid (5 μL, 1.85 kBq, 1 nmol) were added, and incubation was continued for additional 6 hours.

The supernatant of the culture was removed, and after 0.1% SDS-Tris/HCl (pH 7.5, 120 μL) was added for lysis of the cells, neutral fat in the cells was extracted by the Bligh & Dyer method. After the extract was concentrated, it was spotted on a TLC (silica gel plate, Merck, 0.5 mm in thickness) and developed with a solvent of hexane/diethyl ether/acetic acid (70:30:1, v/v/v), and the quantity of isolated [$^{14}$C] triacylglycerols was determined with BAS 2000 (Fuji Film). As a result, substance FKI-3864 inhibited the formation of [$^{14}$C] triacylglycerols, and its value of $IC_{50}$ was measured as being 0.093 μM.

Example 2

Preparation of Substances FKI-3864-1 and FKI-3864-2

15 mg of substance FKI-3864 was dissolved in a small amount of methanol and purified by preparative HPLC (column: Devolosil C30, 4.5φ×250 mm, Nomura Chemical). An isocratic mixed solvent of 85% acetonitrile-0.05% $H_3PO_4$ aqueous solution was used as a mobile phase, and UV absorption at 270 nm of the eluate was monitored at a flow rate of 0.8 mL/min. The eluates of peaks having retention times of 11 min and 13 min were each collected, and the collected solutions were separately concentrated at a reduced pressure, and the remaining aqueous solutions were extracted with ethyl acetate to isolate FKI-3864-1 in a yield of 5.0 mg and FKI-3864-2 in a yield of 7.0 mg, both as a yellow powder.

(Test 2)

Using the same manner as in Test 1, the inhibitory activities on the synthesis of intracellular triacylglycerols of substances FKI-3864-1 and FKI-3864-2 were measured. As a result, the value of $IC_{50}$ of substance FKI-3864-1 was measured as being at least 12 μM and that of substance FKI-3864-2 was measured as being 0.54 μM. In addition, the activities of mixtures in which substances FKI-3864-1 and FKI-3864-2 were mixed at different ratios are shown in Table 2. A 1:1 mixture showed the strongest activity ($IC_{50}$: 0.054 μM).

TABLE 2

Inhibitory activity on the synthesis of intracellular triacylglycerols

| Mixing ratio (3864-1:3864-2) | $IC_{50}$ (μM) |
|---|---|
| 5:1 | >1.2 |
| 4:1 | >1.2 |
| 3:1 | >1.2 |
| 2:1 | >1.2 |
| 1:1 | 0.054 |
| 1:2 | 0.073 |
| 1:3 | 0.16 |
| 1:4 | 0.196 |
| 1:5 | 0.129 |
| 1:8 | 0.247 |
| 1:10 | 0.242 |
| 1:15 | 0.349 |

The invention claimed is:
1. Substance FKI-3864 which is a compound having the following formula [I]:

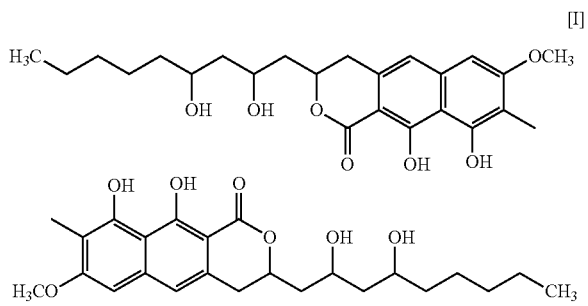

wherein said compound has:
(a) a specific rotation $[\alpha]_D^{26}$ +65.6° (c=0.1, methanol);
(b) a solubility in solvents as follows: soluble in methanol, chloroform, and ethyl acetate; insoluble in water;
(c) hydrogen chemical shifts (ppm) measured in deuterochloroform using a 600 MHz nuclear magnetic resonance spectrometer $\delta_H$: 0.89 (3H), 1.30 (6H), 1.49 (2H), 1.63 (2H), 1.88 (1H), 2.13 (1H), 3.09 (2H), 3.83 (3H), 3.92 (1H), 4.20 (1H), 4.87 (1H), 6.70 (1H), 6.96 (1H), 9.67 (1H) ppm; and
(d) carbon chemical shifts (ppm) measured in deuterochloroform using a 600 MHz nuclear magnetic resonance spectrometer $\delta_C$: 14.0, 22.6, 24.9, 31.7, 32.8, 38.3, 42.3, 42.9, 55.9, 69.5, 73.2, 78.1, 98.1, 99.3, 108.2, 108.4, 116.2, 132.7, 140.1, 155.4, 161.5, 162.8, 171.3 ppm.

2. The substance FKI-3864 as recited in claim 1 which is a compound having the following formula [II] or a compound having the following formula [III] or a mixture of both:

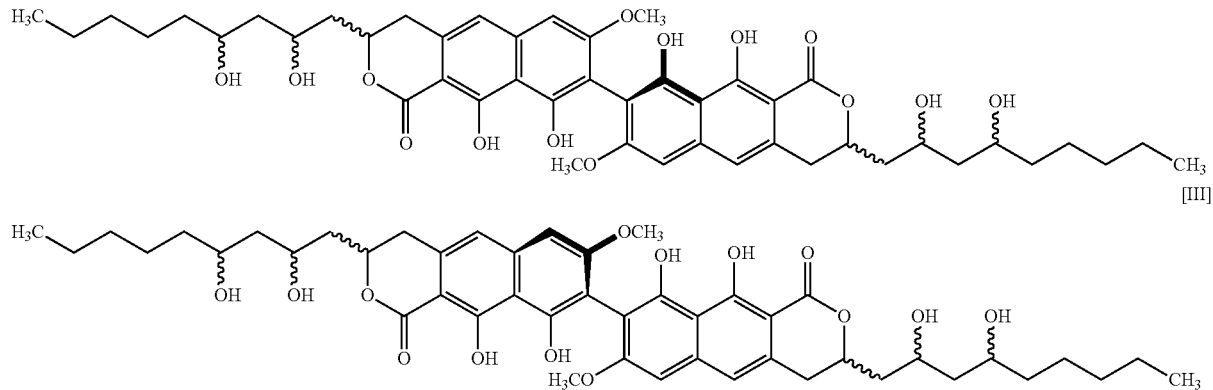

wherein said compound having the formula [II] has:
(a) a specific rotation $[\alpha]_D^{26}$ −190.1° (c=0.1, methanol);
(b) a solubility in solvents as follows: soluble in methanol, chloroform, and ethyl acetate; insoluble in water;
(c) hydrogen chemical shifts (ppm) measured in deuterochloroform using a 600 MHz nuclear magnetic resonance spectrometer $\delta_H$: 0.90 (3H), 1.30 (6H), 1.49 (2H), 1.63 (2H), 1.89 (1H), 2.14 (1H), 3.10 (2H), 3.84 (3H), 3.93 (1H), 4.22 (1H), 4.88 (1H), 6.71 (1H), 6.97 (1H), 9.68 (1H) ppm;
(d) carbon chemical shifts (ppm) measured in deuterochloroform using a 600 MHz nuclear magnetic resonance spectrometer $\delta_C$: 14.0, 22.6, 24.9, 31.7, 33.0, 38.4, 42.2, 42.9, 55.9, 69.6, 73.3, 78.2, 98.1, 99.3, 108.2, 108.4, 116.2, 132.7, 140.1, 155.4, 161.5, 162.9, 171.3 ppm; and
(e) a circular dichroism spectrum: μext (MeOH, Δε): 280 (−71), 251 (+85);
and wherein said compound having the formula [III] has:
(a) a specific rotation $[\alpha]_D^{26}$ +246.3° (c=0.1, methanol);
(b) a solubility in solvents as follows: soluble in methanol, chloroform, and ethyl acetate; insoluble in water;
(c) hydrogen chemical shifts (ppm) measured in deuterochloroform using a 600 MHz nuclear magnetic resonance spectrometer $\delta_H$ 0.90 (3H), 1.30 (6H), 1.49 (2H), 1.63 (2H), 1.88 (1H), 2.14 (1H), 3.10 (2H), 3.85 (3H), 3.92 (1H), 4.20 (1H), 4.88 (1H), 6.71 (1H), 6.97 (1H), 9.67 (1H) ppm;
(d) carbon chemical shifts (ppm) measured in deuterochloroform using a 600 MHz nuclear magnetic resonance spectrometer $\delta_C$: 14.0, 22.6, 24.9, 31.7, 32.8, 38.4, 42.1, 42.9, 56.0, 69.5, 73.4, 78.1, 98.1, 99.3, 108.2, 108.4, 116.3, 132.7, 140.1, 155.4, 161.5, 162.8, 171.3 ppm; and
(e) a circular dichroism spectrum: λext (MeOH, Δε): 278 (+48), 255 (−69).

3. An inhibitory agent which inhibits the synthesis of intracellular triacylglycerols comprising as an active ingredient the substance as recited in claim 1.

4. A pharmaceutical formulation for treatment of obesity comprising as an active ingredient the substance as recited in claim 1.

5. An inhibitory agent which inhibits the synthesis of intracellular triacylglycerols comprising as an active ingredient the substance as recited in claim 2.

6. A pharmaceutical formulation for treatment of obesity comprising as an active ingredient the substance as recited in claim 2.

\* \* \* \* \*

UNITED STATES PATENT AND TRADEMARK OFFICE
CERTIFICATE OF CORRECTION

PATENT NO. : 8,378,125 B2
APPLICATION NO. : 12/867435
DATED : February 19, 2013
INVENTOR(S) : Hiroshi Tomoda et al.

It is certified that error appears in the above-identified patent and that said Letters Patent is hereby corrected as shown below:

In the Claims:

Column 13, Line 36, Claim 2, delete "$\mu$ext" and insert -- $\lambda$ext --

Column 14, Line 21, Claim 2, delete "$\delta_H 0.90$" and insert -- $\delta_H$: 0.90 --

Signed and Sealed this
Seventh Day of May, 2013

Teresa Stanek Rea
*Acting Director of the United States Patent and Trademark Office*

UNITED STATES PATENT AND TRADEMARK OFFICE
CERTIFICATE OF CORRECTION

PATENT NO.        : 8,378,125 B2
APPLICATION NO.   : 12/867435
DATED             : February 19, 2013
INVENTOR(S)       : Tomoda et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 183 days.

Signed and Sealed this
First Day of September, 2015

Michelle K. Lee
*Director of the United States Patent and Trademark Office*